US00PP31247P2

(12) United States Plant Patent
Beekenkamp

(10) Patent No.: US PP31,247 P2
(45) Date of Patent: Dec. 17, 2019

(54) ***OSTEOSPERMUM* PLANT NAMED 'BKOSTOR'**

(50) Latin Name: *Osteospermum ecklonis*
Varietal Denomination: BKOSTOR

(71) Applicant: Annie Cornelia Beekenkamp, Maasdijk (NL)

(72) Inventor: Annie Cornelia Beekenkamp, Maasdijk (NL)

(73) Assignee: Beekenkamp Plants B.V., Maasdijk (NL)

( * ) Notice: Subject to any disclaimer, the term of this patent is extended or adjusted under 35 U.S.C. 154(b) by 0 days.

(21) Appl. No.: 16/350,731

(22) Filed: Dec. 27, 2018

(51) Int. Cl.
*A01H 5/02* (2018.01)
*A01H 6/14* (2018.01)

(52) U.S. Cl.
USPC ..... Plt./360
CPC ..... *A01H 6/14* (2018.05)

(58) Field of Classification Search
USPC ..... Plt./360
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Osteospermum* plant named 'BKOSTOR', characterized by its upright to outwardly spreading and mounding plant habit; moderately vigorous growth rate; freely branching growth habit; dark green-colored leaves; freely flowering habit; daisy-type inflorescences with yellow-colored ray florets with greyed orange-colored longitudinal stripes; and good garden performance.

2 Drawing Sheets

Botanical designation: *Osteospermum ecklonis.*
Cultivar denomination: 'BKOSTOR'.

BACKGROUND OF THE INVENTION

The present invention relates to a new and distinct cultivar of *Osteospermum* plant, botanically known as *Osteospermum ecklonis* and hereinafter referred to by the name 'BKOSTOR'.

The new *Osteospermum* plant is a product of a planned breeding program conducted by the Inventor in Odense, Denmark. The objective of the program is to create and develop new *Osteospermum* plants with uniformly mounded plant habit, freely flowering habit and attractive ray and disc floret coloration.

The new *Osteospermum* plant originated from a cross-pollination by the Inventor in June, 2014 of a proprietary selection of *Osteospermum ecklonis* identified as code number 12-0002-01, not patented, as the female, or seed, parent with a proprietary selection of *Osteospermum ecklonis* identified as code number 15-0171-01, not patented, as the male, or pollen, parent. The new *Osteospermum* plant was discovered and selected by the Inventor as a single flowering plant within the progeny of the stated cross-pollination in a controlled greenhouse environment in Odense, Denmark in July, 2015.

Asexual reproduction of the new *Osteospermum* plant by terminal cuttings in a controlled greenhouse environment in Odense, Denmark since November, 2015 has shown that the unique features of this new *Osteospermum* plant are stable and reproduced true to type in successive generations.

SUMMARY OF THE INVENTION

Plants of the new *Osteospermum* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'BKOSTOR'. These characteristics in combination distinguish 'BKOSTOR' as a new and distinct *Osteospermum* plant:

1. Upright to outwardly spreading and mounding plant habit.
2. Moderately vigorous growth rate.
3. Freely branching growth habit.
4. Dark green-colored leaves.
5. Freely flowering habit.
6. Daisy-type inflorescences with yellow-colored ray florets with greyed orange-colored longitudinal stripes.
7. Good garden performance.

Plants of the new *Osteospermum* differ primarily from plants of the female parent selection in ray floret color. Plants of the new *Osteospermum* have yellow-colored ray florets with greyed orange-colored longitudinal stripes whereas plants of the female parent selection have clear yellow-colored ray florets.

Plants of the new *Osteospermum* differ primarily from plants of the male parent selection in ray floret color. Plants of the new *Osteospermum* have yellow-colored ray florets with greyed orange-colored longitudinal stripes whereas plants of the male parent selection have light yellow-colored ray florets with darker yellow-colored centers.

Plants of the new *Osteospermum* can be compared to plants of the *Osteospermum ecklonis* 'Sunny Cilia', not patented. In side-by-side comparisons, plants of the new *Osteospermum* differ from plants of 'Sunny Cilia' in the following characteristics:

1. Plants of the new *Osteospermum* are more vigorous than and not as compact as plants of 'Sunny Cilia'.

2. Plants of the new *Osteospermum* are freely branching than plants of 'Sunny Cilia'.
3. Plants of the new *Osteospermum* flower later than plants of 'Sunny Cilia'.
4. Plants of the new *Osteospermum* and 'Sunny Cilia' differ in ray floret color as plants of the new *Osteospermum* have yellow-colored ray florets with greyed orange-colored longitudinal stripes whereas plants of 'Sunny Cilia' have orange-colored ray florets.

BRIEF DESCRIPTION OF THE PHOTOGRAPHS

The accompanying photographs illustrate the overall appearance of the new *Osteospermum* plant showing the colors as true as it is reasonably possible to obtain in colored reproductions of this type. Colors in the photographs may differ slightly from the color values cited in the detailed botanical description which accurately describe the colors of the new *Osteospermum* plant.

The photograph on the first sheet comprises a side perspective view of a typical flowering plant of 'BKOSTOR' grown in a container.

The photograph on the second sheet is a close-up view of a typical inflorescence of 'BKOSTOR'.

DETAILED BOTANICAL DESCRIPTION

The aforementioned photographs, following observations and measurements describe plants grown during the spring and summer in 9-cm containers in a glass-covered greenhouse in Odense, Denmark and under cultural practices typical of commercial *Osteospermum* production. During the production of the plants, day temperatures ranged from 14° C. to 20° C. and night temperatures averaged 14° C. Plants were pinched one time and were 14 weeks old when the photographs and description were taken. In the following description, color references are made to The Royal Horticultural Society Colour Chart, 2015 Edition, except where general terms of ordinary dictionary significance are used.

Botanical classification: *Osteospermum ecklonis* 'BKOSTOR'.

Parentage:

*Female, or seed, parent*.—Proprietary selection of *Osteospermum ecklonis* identified as code number 12-0002-01, not patented.

*Male, or pollen, parent*.—Proprietary selection of *Osteospermum ecklonis* identified as code number 15-0171-01, not patented.

Propagation:

*Type*.—Terminal vegetative cuttings.

*Time to initiate roots, summer*.—About twelve days at temperatures about 18° C.

*Time to initiate roots, winter*.—About 14 days at temperatures about 18° C. to 20° C.

*Time to produce a rooted cutting, summer*.—About 20 days at temperatures about 18° C. to 20° C.

*Time to produce a rooted cutting, winter*.—About 28 days at temperatures about 18° C.

*Root description*.—Medium in thickness, fibrous; typically whitish in color, actual color of the roots is dependent on substrate composition, water quality, fertilizers, substrate temperature and physiological age of roots.

*Rooting habit*.—Freely branching; medium density.

Plant description:

*Plant and growth habit*.—Upright to outwardly spreading and mounding plant habit; close to globular to broadly obovate in overall shape; inflorescences positioned above and beyond the foliar plane on moderately strong peduncles; moderately vigorous growth habit; moderate growth rate.

*Plant height, soil level to top of foliar plane*.—About 15.4 cm.

*Plant height, soil level to top of floral plane*.—About 19.3 cm.

*Plant diameter*.—About 21.3 cm.

*Lateral branches*.—Quantity per plant: Freely branching habit with about five primary branches developing per plant, primary branches each with about three secondary branches; pinching enhances branching potential. Length: About 12.9 cm. Diameter: About 4 mm. Internode length: About 6 mm. Strength: Moderately strong. Aspect: Primary branches, about 45° from vertical; secondary branches about 30° from primary branch axis. Texture and luster: Sparsely to moderately pubescent; moderately glossy. Color, developing: Close to 145A to 145B. Color, fully developed: Close to 143C.

*Leaf description*.—Arrangement: Alternate, simple; sessile. Length: About 6.1 cm. Width: About 2.4 cm. Shape: Obovate; moderately concave. Apex: Obtuse to bluntly acute. Base: Long attenuate. Margin: Mostly entire with shallow and divergent lobes; slightly undulate. Texture and luster, upper surface: Smooth, glabrous; sparsely to moderately pubescent along margins; matte. Texture and luster, lower surface: Rough, sparsely to moderately pubescent; matte. Venation pattern: Pinnate, arcuate. Color: Developing leaves, upper surface: Close to between 141A and 143A. Developing leaves, lower surface: Close to 143B. Fully expanded leaves, upper surface: Close to NN137A; venation, close to 138B. Fully expanded leaves, lower surface: Close to 137B; venation, close to 138B.

Inflorescence description:

*Appearance*.—Daisy-type inflorescence form with oblanceolate-shaped ray florets; inflorescences terminal and axillary and positioned above and beyond the foliar plane on moderately strong peduncles; disc and ray florets developing acropetally on a capitulum; inflorescences face mostly upright to slightly outwardly.

*Flowering habit*.—Freely flowering habit with about 20 inflorescences developing per plant.

*Fragrance*.—None detected.

*Flowering response*.—In Denmark, plants of the new *Osteospermum* flower continuously from autumn into the winter; plants begin flowering about ten to twelve weeks after pinching.

*Inflorescence longevity*.—Inflorescences of plants of the new *Osteospermum* last about ten days on the plant; inflorescences persistent.

*Inflorescence buds*.—Height: About 1.2 cm. Diameter: About 1.3 cm. Shape: Roughly globular. Texture and luster: Immature ray florets, smooth and glabrous; immature involucral bracts, moderately pubescent; matte. Color: Immature ray florets, close to 150A to 150B; immature involucral bracts, close to 138B.

*Inflorescence size*.—Diameter: About 6.1 cm. Depth (height): About 1.7 cm. Disc diameter: About 1.7 cm.

*Receptacles*.—Diameter: About 3 mm. Height: About 2 mm. Shape: Reniform. Color: Close to 157A.

*Ray florets*.—Quantity per inflorescence and arrangement: About 25 to 32 ray florets arranged in about two whorls. Length: About 2.8 cm. Width: About 1 cm. Shape: Oblanceolate; slightly carinate. Apex: Shallowly and finely praemorse. Base: Attenuate. Margin: Entire; not undulate. Aspect: Slightly upright; slightly to moderately reflexed. Texture and luster, upper surface: Smooth, glabrous; velvety; matte. Texture and luster, lower surface: Smooth, glabrous; slightly velvety; moderately glossy. Color: When opening, upper surface: Close to between 12A to 13B; fading towards the base to close to 9C. When opening, lower surface: Close to 3B; venation, close to N144C and close to 197B to 197C. Fully opened, upper surface: Close to 12B to 12C; distally flushed and longitudinally striped with close to 166D and N167C; towards the base, close to N170B; venation, similar to lamina color; color does not change with development. Fully opened, lower surface: Close to 165C; longitudinal stripes, close to 172B; venation, close to 166C; color does not change with development.

*Disc florets*.—Quantity per inflorescence and arrangement: About 150 disc florets spirally arranged in about five whorls at the center of the receptacle. Length: About 8 mm. Diameter, apex: About 2.5 mm. Diameter, base: About 1 mm. Shape: Tubular; apex dentate, five-pointed. Texture and luster, inner surface: Smooth, glabrous; glossy. Texture and luster, outer surface: Sparsely pubescent; glossy. Color, immature, inner and outer surfaces: Apex: Close to 146D; tip, close to 202A. Mid-section and base: Close to 157D. Color, mature, inner and outer surfaces: Apex: Close to 153D; tip, close to 148A. Mid-section: Close to 150D. Base: Close to 157D.

*Phyllaries*.—Quantity per inflorescence and arrangement: About 32 phyllaries arranged in about two whorls. Length: About 9 mm. Width: About 1 mm. Shape: Lanceolate. Apex: Narrowly acute. Base: Cuneate. Margin: Entire. Texture and luster, upper surface: Smooth, glabrous; moderately glossy. Texture and luster, lower surface: Moderately pubescent; matte. Color, upper surface: Close to 138C; venation, close to 138A. Color, lower surface: Close to 138A.

*Peduncles*.—Length: About 3.1 cm. Diameter: About 2 mm. Strength: Moderately strong. Aspect: Mostly upright. Texture and luster: Moderately to densely pubescent; moderately glossy. Color: Close to 144A to 144B.

*Reproductive organs*.—Androecium: Present on disc florets only. Quantity per floret: About five. Filament length: About 3 mm. Filament color: Close to N157D. Anther shape: Narrowly oblong. Anther size: About 2 mm by 0.5 mm. Anther color: Close to darker than 200A. Pollen amount: Abundant. Pollen color: Close to 25A. Gynoecium: Present on ray and disc florets. Pistil length: About 4 mm. Stigma diameter: About 2 mm. Stigma shape: Cleft. Stigma color: Close to 200A. Style length: About 2.5 mm. Style color: Close to 200A. Ovary color: Close to 157D.

*Seeds and fruits*.—To date, seed and fruit development has not been observed on plants of the new *Osteospermum*.

Pathogen & pest resistance: To date, plants of the new *Osteospermum* have not been shown to be resistant to pathogens and pests common to *Osteospermum* plants.

Garden performance: Plants of the new *Osteospermum* have been observed to have good garden performance and to tolerate rain, wind, high temperatures about 35° C. and to be suitable for USDA Hardiness Zones 9 to 11.

It is claimed:

1. A new and distinct *Osteospermum* plant named 'BKOSTOR' as illustrated and described.

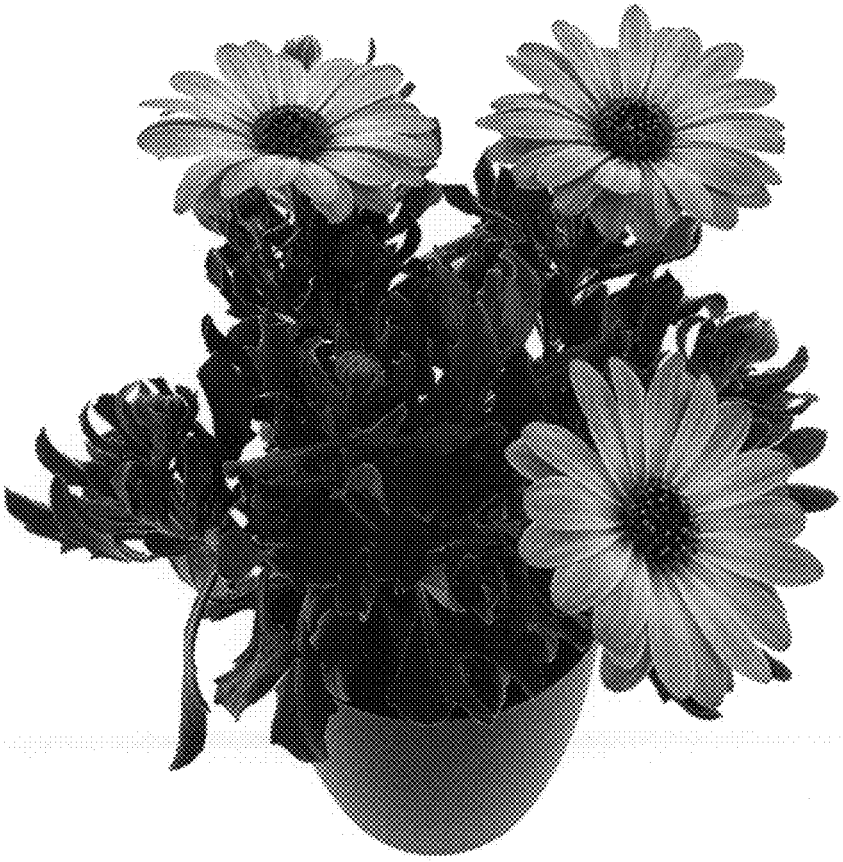

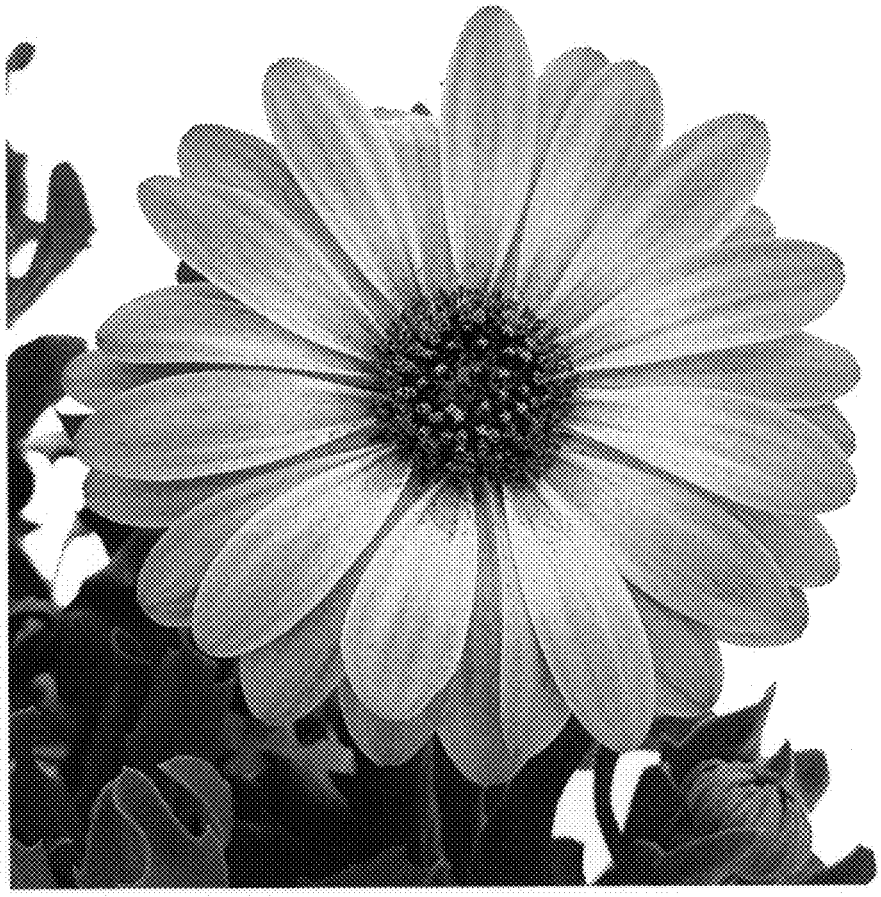

* * * * *